United States Patent [19]

Gergely et al.

[11] Patent Number: 4,762,702
[45] Date of Patent: Aug. 9, 1988

[54] PHARMACEUTICAL PREPARATION CONTAINING IBUPROFEN AND A PROCESS FOR ITS PREPARATION

[76] Inventors: Gerhard Gergely; Thomas Gergely; Irmgard Gergely, all of Gartengasse 8, A-1050 Vienna, Austria

[21] Appl. No.: 794,636

[22] Filed: Nov. 4, 1985

[30] Foreign Application Priority Data

Nov. 5, 1984 [DE] Fed. Rep. of Germany ....... 3440288

[51] Int. Cl.$^4$ ............................................. A61K 9/46
[52] U.S. Cl. .................... 424/44; 424/489; 424/500; 424/501; 514/570
[58] Field of Search ................. 424/44, 489, 500, 501; 514/570

[56] References Cited

U.S. PATENT DOCUMENTS

| | | | |
|---|---|---|---|
| 3,676,549 | 7/1972 | Higuchi | 424/44 |
| 3,764,668 | 10/1973 | Higuchi | 424/44 |
| 3,772,430 | 11/1973 | Blonde | 424/44 |
| 3,773,922 | 11/1973 | Gergely | 424/44 |
| 3,875,073 | 4/1975 | Deininger et al. | 424/44 |
| 3,882,228 | 5/1975 | Boncey et al. | 424/44 |
| 3,887,700 | 6/1975 | Boncey et al. | 424/44 |
| 4,344,929 | 8/1982 | Bonsen et al. | 424/44 |
| 4,344,934 | 8/1982 | Martin et al. | 424/501 |
| 4,417,993 | 11/1983 | Gergely | 424/44 |
| 4,540,602 | 9/1985 | Motoyama et al. | 424/496 |
| 4,593,020 | 6/1986 | Guinot | 514/159 |
| 4,613,497 | 9/1986 | Chavkin | 424/44 |
| 4,614,648 | 9/1986 | Bru | 424/44 |
| 4,678,661 | 7/1987 | Gergely et al. | 424/44 |

FOREIGN PATENT DOCUMENTS

| | | | |
|---|---|---|---|
| 55-01244 | 1/1980 | Japan | 514/570 |
| 55-92341 | 7/1980 | Japan | 514/570 |
| 56-46837 | 4/1981 | Japan | 514/570 |
| 56-46838 | 4/1981 | Japan | 514/570 |
| 56-46839 | 4/1981 | Japan | 514/570 |
| 56-34618 | 4/1981 | Japan | 514/570 |
| 58-198417 | 11/1983 | Japan | 514/570 |
| WO86/02834 | 5/1986 | PCT Int'l Appl. | 514/570 |
| 970462 | 9/1964 | United Kingdom . | |

OTHER PUBLICATIONS

Kowa II, CA., 95 #156580m (1981) of JPN 81 46837, 28 Apr. 1981.
Chow, CA., 105 #48887h (1986) of Int. J. Pharm. 28(2–3), 95–101 (1986).
Hayashi, CA., 94 #90331b (1981) of JPN 80 01,244, 12 Jan. 1980.
Corrigan, CA., 103 #76147u (1985) of Drug Dev. Ind. Pharm. 11(2–3): 677–695 (1985).
Kurozumi, CA., 84 #111578y (1976) of Chem. Pharm. Bull., 23(12): 30628 (1978).

*Primary Examiner*—Shep K. Rose
*Attorney, Agent, or Firm*—Marmorek, Guttman & Rubenstein

[57] ABSTRACT

A pharmaceutical preparation containing ibuprofen is disclosed. In the preparation, the ibuprofen particles are enveloped by a coating of a hydro-colloid and fumaric acid. Preferably, the hydro-colloid comprises xanthan gum and/or maltodextrin. This preparation reduces the tendency of ibuprofen to irritate the esophagus and the gastrointestinal tract when taken orally. An effervescent mixture of the ibuprofen containing preparation can be prepared by incorporating citric acid and calcium carbonate into the mixture. A process for the manufacture of the ibuprofen containing preparation is also disclosed. In this process, ibuprofen particles are coated with the hydro-colloid and fumaric acid under vacuum conditions in a vacuum mixing machine and the resulting preparation is thereafter vacuum-dried.

8 Claims, No Drawings

PHARMACEUTICAL PREPARATION CONTAINING IBUPROFEN AND A PROCESS FOR ITS PREPARATION

BACKGROUND OF THE INVENTION

This invention relates to an ibuprofen containing pharmaceutical preparations. More particularly, this invention relates to an ibuprofen containing pharmaceutical preparation in which the unpleasant taste of ibupofen is avoided, and in which the tendency of the ibuprofen to irritate the esophagus and the gastrointestinal tract is reduced by coating the ibuprofen particles with a hydro-colloid and fumaric acid. This invention further relates to a process for manufacturing the ibuprofen containing pharmaceutical preparation.

Pharmaceutical preparations are known which contain as inactive agents substances having an acid or an acid radical. Such substances have a tendency to irritate strongly the mucous membrane of the mouth and throat. One such active agent which is known to irritate strongly the mucous membranes of the mouth and throat is ibuprofen (2-(4-isobutyl phenyl) propionic acid).

Ibuprofen is an active agent which has become increasingly important for the treatment of rheumatism and arthritis. It is relatively insoluble in water. It also has a very unpleasant taste, and, as mentioned above, causes irritation of the mucous membranes of the esophagus. It is also known from the literature that, like aspirin, ibuprofen can cause gastrointestinal bleeding. This occurs if the substance arrives at the stomach wall in a relatively high concentration, such as in the form of a tablet or a capsule.

This problem can be alleviated if the ibuprofen were suspended in water prior to its being taken orally, thus preventing local over-concentration from developing in the gastrointestinal tract. However, because of the relative insolubility of ibuprofen, such water suspensions are difficult to prepare.

Known water suspensions of ibuprofen contain discrete particles of ibuprofen. These particles may become trapped in the mouth and esophagus where they may cause scratching and irritating sensations. They also impart an unpleasant taste to the suspension. There have thus been difficulties heretofore associated with the oral administration of ibuprofen containing substances.

It is therefore an object of the present invention to provide an ibuprofen containing pharmaceutical preparation which does not irritate the mucous membranes of the throat and gastrointestinal tract.

It is also an object of the present invention to provide an ibuprofen containing pharmaceutical preparation which does not have the unpleasant taste effects of prior art ibuprofen containing preparations.

It is also an object of the present invention to prepare an effervescent mixture of an ibuprofen containing pharmaceutical preparation.

It is yet another object of the present invention to provide a process for the manufacture of the ibuprofen containing pharmaceutical preparation.

SUMMARY OF THE INVENTION

These and other objects are achieved by means of an ibuprofen containing pharmaceutical preparation wherein the ibuprofen particles are coated with a hydro-colloid and with fumaric acid. Desirably, the hydro-colloid contains xanthan gum and/or maltodextrin.

The ibuprofen containing pharmaceutical preparation of the present invention can be prepared, if desired, in the form of an effervescent mixture. Such a mixture can be manufactured by adding citric acid and calcium carbonate to the previously prepared ibuprofen coated preparation. In such an effervescent mixture, the calcium carbonate envelops the citric acid and a bonding layer is formed by the reaction of the calcium carbonate with the surface adjacent layer of the citric acid crystal.

In accordance with a different aspect of the present invention, a process for the manufacture of the ibuprofen containing pharmaceutical preparation is provided. In accordance with this process, ibuprofen particles under vacuum conditions are coated with a hydro-colloid and fumaric acid in a vacuum mixing machine, and the resulting mixture is then vacuum-dried. More particularly, a process is provided wherein ibuprofen particles and a hydro-colloid are mixed with water in a vacuum mixing machine at a pressure of about 0.1 bar. The mixture is then partially dried to about 0.2 bar. Fumaric acid is added to the mixture, and the mixture is then completely dried.

The ibuprofen containing preparation pharmaceutical preparation of the present invention does not suffer from the shortcomings of prior art preparations due to the envelopment of the ibuprofen crystals by the hydro-colloid in the presence of fumaric acid. The fumaric acid has a higher pH than the ibuprofen and prevents the negative taste effects. The pseudo-colloid performs the function of connecting the water insoluble ibuprofen particles to the sparingly soluble fumaric acid.

The process by which the ibuprofen containing pharmaceutical preparation of the present invention is prepared may be conveniently and advantageously carried out in a vacuum mixing machine by a process which is generally described in German patent application P 3434774.7, which is incorporated herein by reference.

DETAILED DESCRIPTION OF PREFERRED EMBODIMENTS

The present invention will be more fully illustrated by reference to the following examples.

EXAMPLE 1

200 parts of ibuprofen were treated with a solution of 10 parts xanthan gum and 10 parts maltodextrin in 50 parts of water. 20 parts fumaric acid were added to the mixture prior to complete drying in vacuo at about 200 mbar. After complete drying, a granulate was obtained which was ground to a grain size of about 0.3 mm.

These particles were then combined with crystalline sugar and citric acid by an instantaneous technology. The amount of sugar used was equal to 10 to 15 times the quantity of the pharmaceutical preparation, while the amount of citric acid was equal to twice the quantity of the pharmaceutical preparation.

The resulting mixture could be made into a pleasant tasting beverage having a dosage of 200 mg ibuprofen and which no longer irritated the mucous membranes.

EXAMPLE 2

The mixture of example 1 was successfully prepared as an effervescent mixture by adding citric acid and calcium carbonate.

50 parts citric acid were reacted with 50 parts calcium carbonate in vacuo, 5 parts of 50% ethanol being added. This effervescent mixture was dried and added to the ibuprofen containing pharmaceutical preparation of Example 1 in an amount equal to 5 times the amount of the ibuprofen.

A product thus prepared comprised a slowly effervescing mixture in which the calcium carbonate exerted an additional pleasant tasting effect on the ibuprofen.

While the invention has been described by reference to specific embodiments, this was for purposes for illustration only and should not be construed to limit the spirit or the scope of the invention.

What is claimed is:

1. An ibuprofen containing pharmaceutical preparation for making up an instant drink and comprising a therapeutically effective amount of ibuprofen particles, a hydro-colloid, and fumaric acid, wherein said hydro-colloid and fumaric acid coat said ibuprofen particles.

2. The pharmaceutical preparation of claim 1 wherein said pseudo-colloid contains maltodextrin.

3. The pharmaceutical preparation of claim 1 further comprising an effervescent mixture.

4. The pharmaceutical preparation of claim 3 wherein said effervescent mixture comprises citric acid and calcium carbonate.

5. The pharmaceutical preparation of claim 1, comprising about 200 parts by weight of ibuprofen, 10 parts by weight of xanthan gum, 10 parts by weight of maltodextrin, and 20 parts by weight of fumaric acid.

6. The pharmaceutical preparation of claim 5, further comprising 50 parts by weight of citric acid and 50 parts by weight of calcium carbonate.

7. A process for the manufacture of an ibuprofen containing pharmaceutical preparation, comprising enveloping ibuprofen particles with a coating of a hydro-colloid and fumaric acid under vacuum conditions, and vacuum drying the resulting mixture.

8. A process in accordance with claim 7, wherein said ibuprofen particles and a hydro-colloid are mixed with water under a pressure of about 0.1 bar, said mixture is partially dried to a pressure of about 0.2 bar, fumaric acid is added to this mixture, and the resulting mixture is dried to completion.

* * * * *